(12) United States Patent (10) Patent No.: US 12,033,975 B2
Kobayashi (45) Date of Patent: Jul. 9, 2024

(54) SEMICONDUCTOR DEVICE, ENDOSCOPE, AND METHOD FOR MANUFACTURING SEMICONDUCTOR DEVICE

(71) Applicant: OLYMPUS CORPORATION, Tokyo (JP)

(72) Inventor: Keiichi Kobayashi, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 326 days.

(21) Appl. No.: 17/336,499

(22) Filed: Jun. 2, 2021

(65) Prior Publication Data

US 2021/0288023 A1 Sep. 16, 2021

Related U.S. Application Data

(63) Continuation of application No. PCT/JP2018/044530, filed on Dec. 4, 2018.

(51) Int. Cl.
*H01L 23/00* (2006.01)
*A61B 1/05* (2006.01)
(Continued)

(52) U.S. Cl.
CPC ........ *H01L 24/92* (2013.01); *H01L 23/49811* (2013.01); *H01L 24/24* (2013.01);
(Continued)

(58) Field of Classification Search
CPC ......... H01L 24/24; H01L 24/32; H01L 24/73; H01L 24/82; H01L 24/83; H01L 24/92; H01L 23/49811
(Continued)

(56) References Cited

U.S. PATENT DOCUMENTS

2005/0242408 A1 11/2005 Yang et al.
2007/0012954 A1* 1/2007 Murayama ........ H01L 27/14843
257/222
(Continued)

FOREIGN PATENT DOCUMENTS

EP 2835093 A1 2/2015
JP 2001-16486 A 1/2001
(Continued)

OTHER PUBLICATIONS

International Search Report dated Feb. 26, 2019 issued in PCT/JP2018/044530.

*Primary Examiner* — Jasmine J Clark
(74) *Attorney, Agent, or Firm* — Scully, Scott, Murphy & Presser, P.C.

(57) ABSTRACT

An image pickup apparatus includes: an image pickup member having a first surface and a second surface, an external electrode being disposed on the second surface; a terminal where a core wire terminal is disposed on a first upper surface and a core wire electrode is disposed on a lower surface; a wiring layer including an insulation layer and a wiring, the wiring being in contact with the external electrode and the core wire electrode, a third surface being in contact with the second surface and the lower surface; a resin layer disposed on the third surface, an outer dimension of the resin layer being equal to an outer dimension of the wiring layer, the resin layer fixing the image pickup member and the terminal; and an electric cable including a core wire bonded to the core wire terminal.

20 Claims, 11 Drawing Sheets

(51) Int. Cl.
  *H01L 23/498* (2006.01)
  *H01L 27/146* (2006.01)
  *H04N 23/50* (2023.01)
  *H04N 23/54* (2023.01)

(52) U.S. Cl.
  CPC .............. *H01L 24/73* (2013.01); *H01L 24/82* (2013.01); *H01L 24/83* (2013.01); *H01L 27/14636* (2013.01); *H04N 23/54* (2023.01); *A61B 1/051* (2013.01); *H01L 24/25* (2013.01); *H01L 24/32* (2013.01); *H01L 2224/24011* (2013.01); *H01L 2224/24101* (2013.01); *H01L 2224/24155* (2013.01); *H01L 2224/25175* (2013.01); *H01L 2224/32155* (2013.01); *H01L 2224/73267* (2013.01); *H01L 2224/82005* (2013.01); *H01L 2224/82101* (2013.01); *H01L 2224/82106* (2013.01); *H01L 2224/83005* (2013.01); *H01L 2224/92244* (2013.01); *H04N 23/555* (2023.01)

(58) Field of Classification Search
  USPC ........................................................ 257/434
  See application file for complete search history.

(56) References Cited

U.S. PATENT DOCUMENTS

| 2014/0239330 | A1 | 8/2014 | Obika |
| 2015/0038787 | A1 | 2/2015 | Nishimura |
| 2017/0317130 | A1* | 11/2017 | Yoshida ............ H01L 27/14618 |
| 2018/0168046 | A1 | 6/2018 | Miyawaki |

FOREIGN PATENT DOCUMENTS

| JP | 2005-317887 | A | 11/2005 |
| JP | 2007-287801 | A | 11/2007 |
| JP | 2011-050496 | A | 3/2011 |
| JP | 2013-215309 | A | 10/2013 |
| JP | 2014-164110 | A | 9/2014 |
| JP | 2017-228763 | A | 12/2017 |
| JP | 6393018 | B1 | 9/2018 |
| WO | 2017/037828 | A1 | 3/2017 |
| WO | 2018/186163 | A1 | 10/2018 |

* cited by examiner

SEMICONDUCTOR DEVICE, ENDOSCOPE, AND METHOD FOR MANUFACTURING SEMICONDUCTOR DEVICE

CROSS REFERENCE TO RELATED APPLICATION

This application is a continuation application of PCT/JP2018/044530 filed on Dec. 4, 2018, the entire contents of which are incorporated herein by this reference.

BACKGROUND OF THE INVENTION

1. Field of the Invention

The present invention relates to a semiconductor device where a semiconductor member and an electric cable are connected with each other, to an endoscope including a semiconductor device where a semiconductor member and an electric cable are connected with each other, and to a method for manufacturing the semiconductor device where the semiconductor member and the electric cable are connected with each other.

2. Description of the Related Art

To reduce the diameter of a distal end portion of an endoscope, an image pickup apparatus has been developed which includes an ultra-small image pickup device. The image pickup device is provided with external electrodes that supply drive signals or output image pickup signals. If an electric cable is bonded to the external electrode, the image pickup device may be damaged due to heat or stress generated at the time of bonding the electric cable.

International Publication No. 2017/037828 discloses an image pickup apparatus where an image pickup device is bonded to a wiring board, and an electric cable is bonded to the wiring board.

Japanese Patent Application Laid-Open Publication No. 2007-287801 discloses a hybrid circuit device where a semiconductor module, including a light emitting element device, and an LSI are mounted on a multilayer wiring board. An optical fiber is disposed on the light emitting element device.

SUMMARY OF THE INVENTION

One aspect is directed to a semiconductor device including: a semiconductor member having a first surface and a second surface on an opposite side of the first surface, an external electrode being disposed on the second surface; a terminal member having a first upper surface and a lower surface on an opposite side of the first upper surface, a core wire terminal being disposed on the first upper surface, a core wire electrode being disposed on the lower surface; a wiring layer having a third surface and a fourth surface on an opposite side of the third surface, the wiring layer including an insulation layer and a wiring, the wiring being in contact with the external electrode and the core wire electrode, the third surface being in contact with the second surface of the semiconductor member and the lower surface of the terminal member; a resin layer disposed on the third surface of the wiring layer, an outer dimension of the resin layer being equal to an outer dimension of the wiring layer, the resin layer fixing the semiconductor member and the terminal member in a state where the resin layer does not cover the first surface and the first upper surface; and an electric cable including a core wire bonded to the core wire terminal.

Another aspect is directed to an endoscope including a semiconductor device, wherein the semiconductor device includes: a semiconductor member having a first surface and a second surface on an opposite side of the first surface, an external electrode being disposed on the second surface; a terminal member having a first upper surface and a lower surface on an opposite side of the first upper surface, a core wire terminal being disposed on the first upper surface, a core wire electrode being disposed on the lower surface; a wiring layer having a third surface and a fourth surface on an opposite side of the third surface, the wiring layer including an insulation layer and a wiring, the wiring being in contact with the external electrode and the core wire electrode, the third surface being in contact with the second surface of the semiconductor member and the lower surface of the terminal member; a resin layer disposed on the third surface of the wiring layer, an outer dimension of the resin layer being equal to an outer dimension of the wiring layer, the resin layer fixing the semiconductor member and the terminal member in a state where the resin layer does not cover the first surface and the first upper surface; and an electric cable including a core wire bonded to the core wire terminal.

Yet another aspect is directed to a method for manufacturing a semiconductor device, the method including: temporarily fixing a plurality of semiconductor members and a plurality of terminal members to a first support substrate, each of the plurality of semiconductor members having a first surface and a second surface on an opposite side of the first surface, one or more external electrodes being disposed on the second surface, each of the plurality of terminal members having a first upper surface and a lower surface on an opposite side of the first upper surface, a core wire terminal being disposed on the first upper surface, a core wire electrode being disposed on the lower surface; fixing the plurality of semiconductor members and the plurality of terminal members on the first support substrate by disposing a resin around the plurality of semiconductor members and the plurality of terminal members; separating a main member wafer from the first support substrate, the main member wafer including the plurality of semiconductor members, the plurality of terminal members, and the resin; temporarily fixing, to a second support substrate, at least either of the first surface of each of the plurality of semiconductor members on the main member wafer or the first upper surface of each of the plurality of terminal members on the main member wafer; disposing a plurality of wiring layers including a wiring that connects the external electrode of each of the plurality of semiconductor members with the core wire electrode of each of the plurality of terminal members; separating the main member wafer, including the wiring layer, from the second support substrate; and bonding a core wire of an electric cable to the core wire terminal.

DETAILED DESCRIPTION OF THE PREFERRED EMBODIMENTS

First Embodiment

Figure 1:
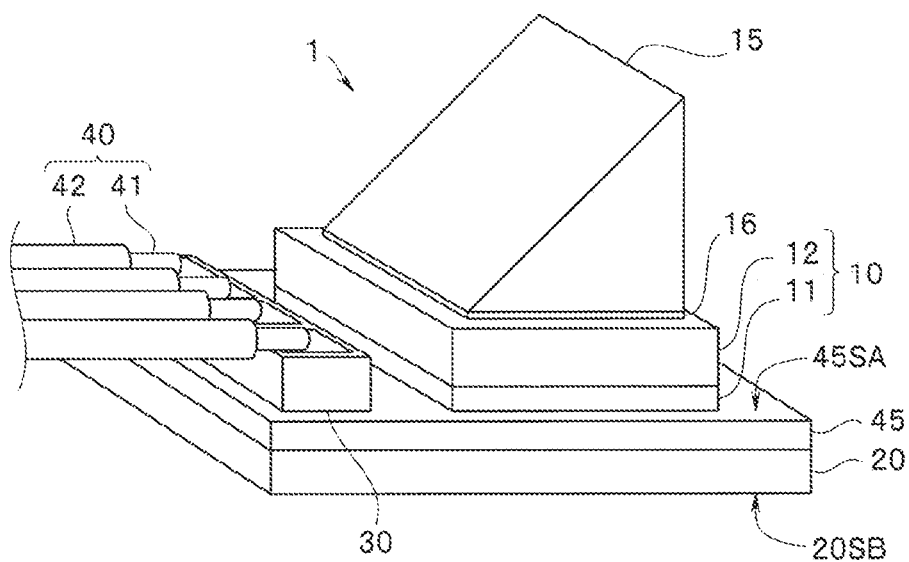
FIG. 1 is a perspective view of a semiconductor device of a first embodiment.
Figure 2:
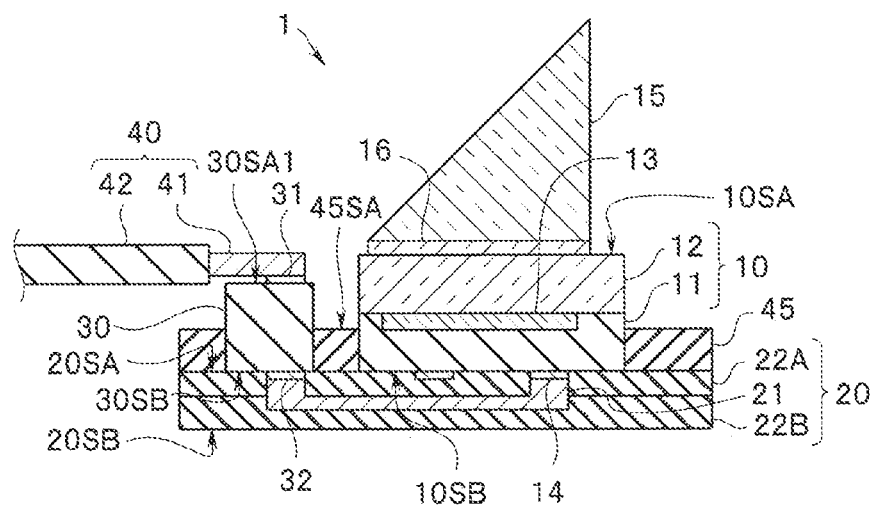
FIG. 2 is a cross-sectional view of the semiconductor device of the first embodiment.
Figure 3:
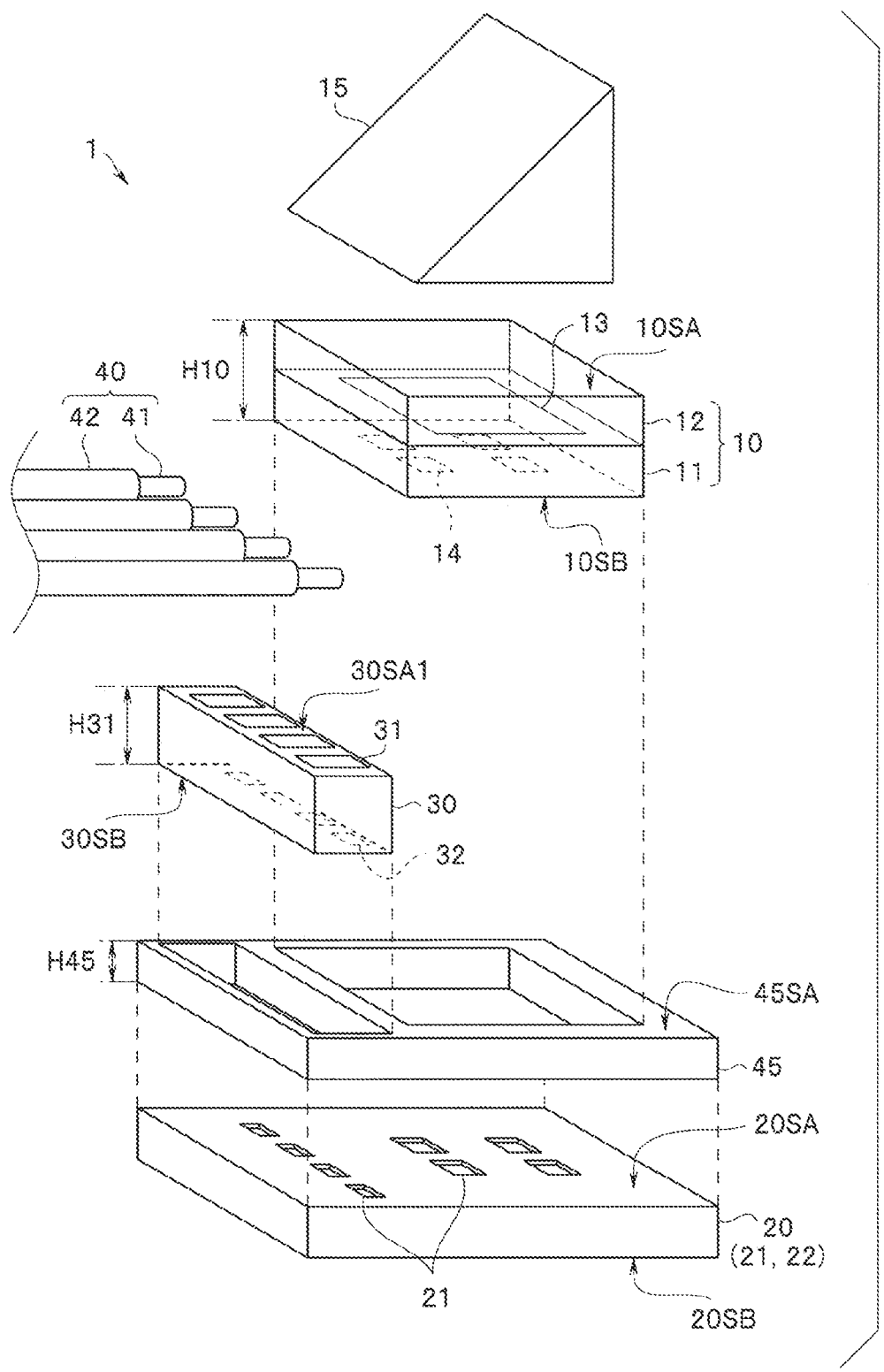
FIG. 3 is an exploded view of the semiconductor device of the first embodiment.
Figure 19:
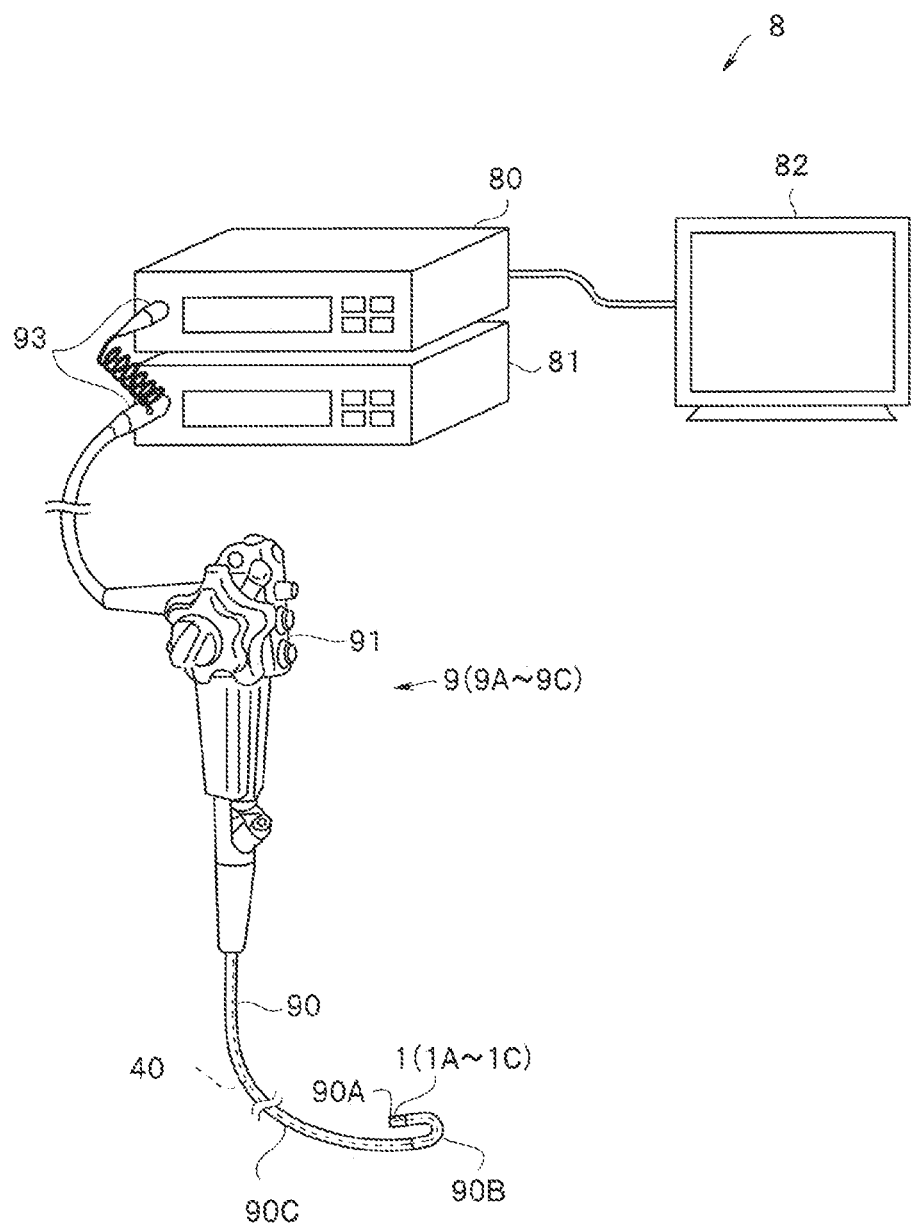
FIG. 19 is a perspective view of an endoscope of a fifth embodiment.

A semiconductor device of the present embodiment shown in FIG. 1, FIG. 2, and FIG. 3 is an image pickup apparatus 1 provided at a distal end portion 90A of an endoscope 9 (see FIG. 19).

A so-called horizontal image pickup apparatus 1 includes an image pickup member 10, which is a semiconductor member, a prism 15, a wiring layer 20, a terminal member 30, electric cables 40, and a resin layer 45.

In the description made hereinafter, drawings based on respective embodiments are schematic views. A relationship between thicknesses and widths of the respective portions, a ratio between thicknesses of the respective portions, and a relative angle between the respective portions, for example, may differ from actual ones. The dimensional relations and the ratio may be different between drawings. Further, the illustration of some constitutional elements and use of reference symbols may be omitted.

The image pickup member 10 includes an image pickup device 11, which is a semiconductor element, and a cover glass 12. The image pickup member 10 has a rectangular parallelepiped shape having a first surface 10SA and a second surface 10SB on the opposite side of the first surface 10SA. A plurality of external electrodes 14 are disposed on the second surface 10SB. A light receiving circuit 13 of the image pickup device 11 is connected with the external electrodes 14 through first through wirings 11X (see FIG. 5), for example. The image pickup device 11 may be either one of a front surface irradiation type image sensor or a back surface irradiation type image sensor.

The prism 15 is caused to adhere to the first surface 10SA by using a transparent adhesive agent 16.

The terminal member 30 has a first upper surface 30SA1 and a lower surface 30SB on the opposite side of the first upper surface 30SA1. The terminal member 30 is a cable connecting member where a plurality of core wire terminals (connection lands) 31 are disposed on the first upper surface 30SA1, and a plurality of core wire electrodes 32 are disposed on the lower surface 30SB. The core wire terminals 31 and the core wire electrodes 32 are connected with each other through second through wirings 30X (see FIG. 5), for example.

The wiring layer 20 is a wiring member having a third surface 20SA and a fourth surface 20SB on the opposite side of the third surface 20SA, the wiring layer 20 including insulation layers 22 (22A, 22B) and wirings 21. The third surface 20SA is in contact with the second surface 10SB of the image pickup member 10 and the lower surface 30SB of the terminal member 30.

Each electric cable 40 includes a core wire 41 and a first cover layer 42 that covers the core wire 41. The core wire 41 is bonded to the core wire terminal 31 of the terminal member 30 using a solder, for example. The core wire 41 is electrically connected with the light receiving circuit 13 through the core wire terminal 31, the second through wiring 30X, the core wire electrode 32, the wiring 21, and the external electrode 14.

The resin layer 45 is disposed on the third surface 20SA of the wiring layer 20 to fix the image pickup member 10 and the terminal member 30. The resin layer 45 is a fixing portion that fixes the image pickup member 10 and the terminal member 30 to the wiring layer 20 in a state where the resin layer 45 integrally holds the image pickup member 10 and the terminal member 30. A thickness H45 of the resin layer 45 is smaller than the thickness of the terminal member 30 (a length H31 from the first upper surface 30SA1 to the lower surface 30SB). Therefore, the core wire terminals 31 of the terminal member 30 are not covered by the resin layer 45. That is, an upper surface 45SA of the resin layer 45 is located at a position lower than the first surface 10SA and the first upper surface 30SA1 (located at a position close to the third surface 20SA).

The upper surface 45SA of the resin layer 45 is parallel to the third surface 20SA of the wiring layer 20, and the outer dimensions of the upper surface 45SA are equal to the outer dimensions of the third surface 20SA. Therefore, the side surfaces of the resin layer 45 and the corresponding side surfaces of the wiring layer 20 are in the same planes.

In the image pickup apparatus 1, the wirings 21 of the wiring layer 20 are in contact with the external electrodes 14 and the core wire electrodes 32. The wiring layer 20 is a rewiring layer disposed on the resin layer 45 to which the image pickup member 10 and the terminal member 30 are fixed. At least regions of each wiring 21 which are in contact with the external electrode 14 and the core wire electrode 32 are made of a conductive material formed on the front surface of the external electrode 14 and the front surface of the core wire electrode 32. For example, the wiring 21 may be made of a copper sputtered film formed on the external electrode 14 and the core wire electrode 32, or a copper electroplating film formed on a base conductive film.

In the image pickup apparatus 1, the wirings 21 are formed and hence, the wirings 21 are bonded with the external electrodes 14 and the core wire electrodes 32 in a state of contact whereby the wirings 21, the external electrodes 14, and the core wire electrodes 32 are electrically connected with each other. Therefore, the image pickup apparatus 1 can be easily manufactured, and has high reliability for bonding between the wirings 21 and the external electrodes 14 and between the wirings 21 and the core wire electrodes 32.

If the electric cables 40 are bonded to the external electrodes 14 of the image pickup device 11, the image pickup device may be damaged due to heat or stress generated at the time of bonding. Further, if the image pickup device 11 is bonded to a wiring board, the image pickup apparatus has a large thickness.

In the image pickup apparatus 1, the external terminals 14 of the image pickup device 11 are in contact with the wirings 21, and are not bonded using a solder and hence, there is no possibility that the image pickup device 11 is damaged due to heat or stress generated at the time of melting solder, so that reliability of the image pickup apparatus 1 is reduced. Further, the image pickup device 11 is fixed not to a wiring board, but to the resin layer 45 and hence, the image pickup apparatus 1 has a small thickness and a small size.

<Method for Manufacturing Image Pickup Apparatus>

Figure 4:
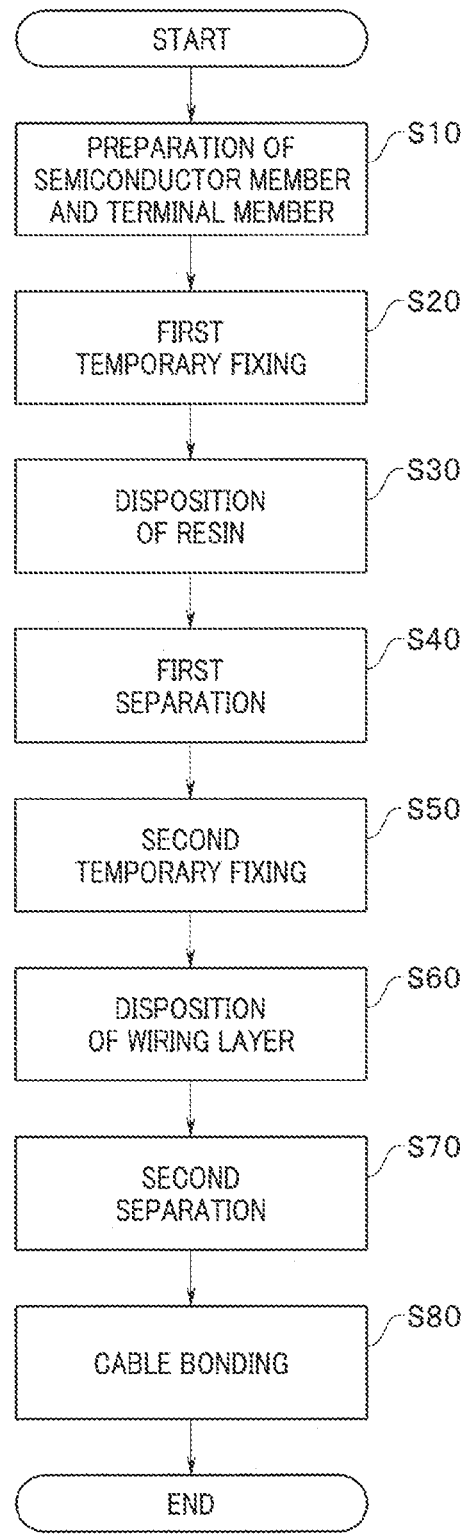
FIG. 4 is a flowchart of a method for manufacturing the semiconductor device of the first embodiment.

A method for manufacturing the image pickup apparatus 1 will be described with reference to a flowchart shown in FIG. 4.

<Step S10> Step of Preparing Semiconductor Member (Image Pickup Member) and Terminal Member Although not shown in the drawing, an image pickup device wafer is prepared by disposing a plurality of light receiving circuits 13 and the like on a silicon wafer by using a known technique for manufacturing a semiconductor. Peripheral circuits may also be formed on the image pickup device wafer, the peripheral circuits performing primary processing on output signals from the light receiving circuits 13 or performing processing on drive control signals.

A glass wafer that protects the light receiving circuits 13 is caused to adhere to the light receiving surface of the image pickup device wafer. External electrodes 14 are disposed on the back surface of the image pickup device wafer, the external electrodes 14 being connected with the light receiving circuits 13 through first through wirings 11X. By cutting the image pickup device wafer to which the glass wafer is caused to adhere, a plurality of image pickup members 10 (image pickup devices 11 to which the cover glasses 12 are caused to adhere) are prepared.

Each terminal member 30 is a three-dimensional wiring board where a base body is made of a resin, ceramic, silicon, or the like. The terminal member 30 may also be a MID (molded interconnect device), which is a three-dimensional component where a conductive pattern is formed on an injection molding product. Core wire terminals 31 and core wire electrodes 32 may be connected with each other through surface wirings.

<Step S20> First Temporary Fixing Step

Figure 5:
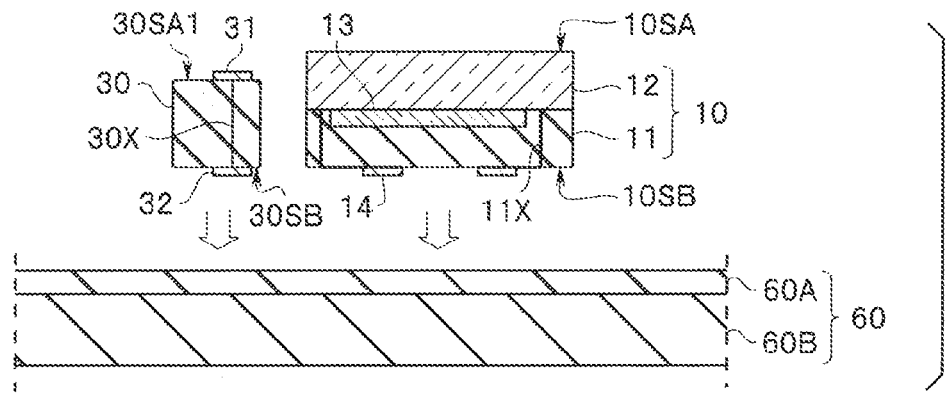
FIG. 5 is a cross-sectional view for describing the method for manufacturing the semiconductor device of the first embodiment.

As shown in FIG. 5, the image pickup member 10 and the terminal member 30 are temporarily fixed to a first support substrate 60 in a state where the image pickup member 10 and the terminal member 30 are disposed at predetermined positions.

In the first support substrate 60, an adhesive layer (temporary fixing layer) 60A is disposed on a base body 60B. The adhesive layer 60A is soft. Therefore, in the case where the external electrodes 14 and the core wire electrodes 32 are protruding electrodes, the external electrodes 14 and the core wire electrode 32 are embedded in the adhesive layer 60A. As will be described later, adhesive strength of the adhesive layer 60A is eliminated by performing ultraviolet irradiation treatment or heat treatment.

Note that the plurality of image pickup members 10 and the plurality of terminal members 30 are temporarily fixed to one first support substrate 60.

<Step S30> Resin Disposing Step

Figure 6:
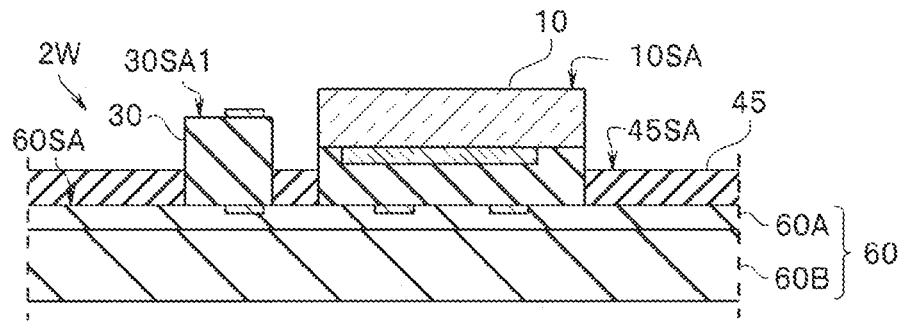
FIG. 6 is a cross-sectional view for describing the method for manufacturing the semiconductor device of the first embodiment.

As shown in FIG. 6, an uncured resin layer 45 is disposed on a main surface 60SA of the first support substrate 60 at positions around the image pickup members 10 and the terminal members 30. By performing curing treatment on the resin layer 45, a main member wafer 2W is prepared where the image pickup members 10 and the terminal members 30 are fixed by the resin layer 45.

For example, an uncured epoxy resin is disposed on the first support substrate 60 and, thereafter, thermosetting treatment is performed. The resin layer 45 is disposed such that the resin layer 45 is prevented from covering first surfaces 10SA of the image pickup members 10 and first upper surfaces 30SA1 of the terminal members 30. Note that the resin layer 45 may completely cover the side surfaces of the image pickup members 10.

<Step S40> First Separation Step

Figure 7:
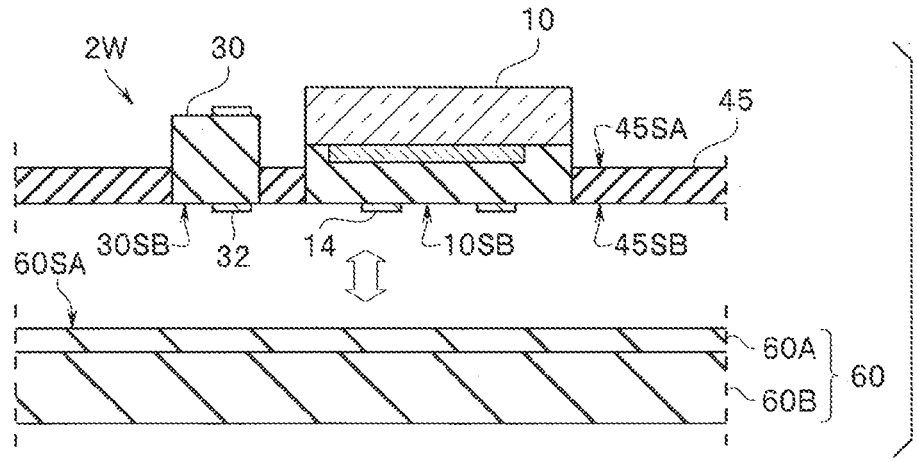
FIG. 7 is a cross-sectional view for describing the method for manufacturing the semiconductor device of the first embodiment.

As shown in FIG. 7, the main member wafer 2W, where the plurality of image pickup members 10 and the plurality of terminal members 30 are fixed by the resin layer 45, is separated from the first support substrate 60. For example, adhesive strength of the adhesive layer 60A is eliminated by performing ultraviolet irradiation treatment and hence, the main member wafer 2W is easily detached from the first support substrate 60.

A lower surface 45SB of the resin layer 45, second surfaces 10SB of the image pickup members 10, and lower surfaces 30SB of the terminal members 30 are located on the same plane. In the case where the external electrodes 14 and the core wire electrodes 32 are protruding electrodes, the external electrodes 14 and the core wire electrodes 32 protrude from a plane that includes the lower surface 45SB of the resin layer 45. In the case where the external electrodes 14 or the core wire electrodes 32 are protruding electrodes, only the protruding electrodes protrude from the plane that includes the lower surface 45SB of the resin layer 45.

<Step S50> Second Temporary Fixing Step

Figure 8:
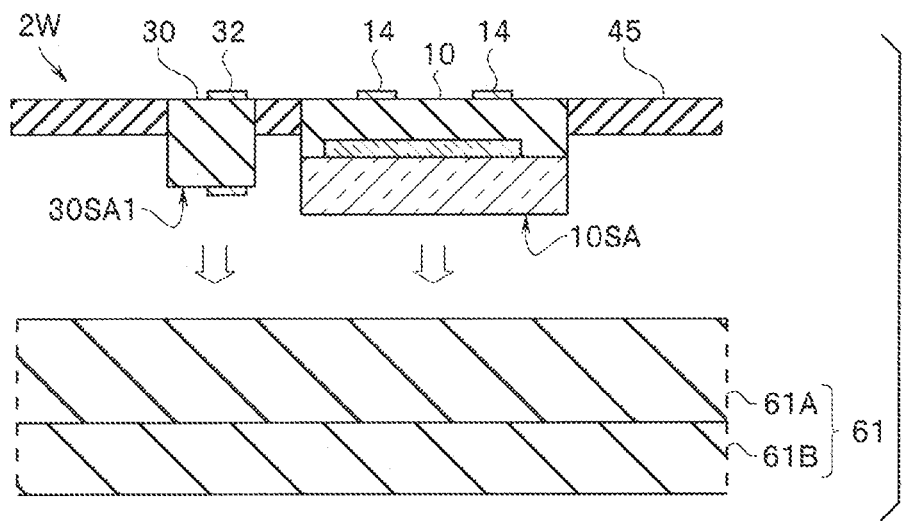
FIG. 8 is a cross-sectional view for describing the method for manufacturing the semiconductor device of the first embodiment.

As shown in FIG. 8, the main member wafer 2W is temporarily fixed to a second support substrate 61. In the second support substrate 61, an adhesive layer 61A is disposed on a base body 61B. The second support substrate 61 may have the same structure as the first support substrate 60, or may have a different structure.

In the case where the height of the terminal members 30 is greater than the height of the image pickup members 10, the first upper surfaces 30SA1 of the terminal members 30 are temporarily fixed to the second support substrate 61. In the case where the height of the terminal members 30 is substantially equal to the height of the image pickup members 10, the first upper surfaces 30SA1 of the terminal members 30 and the first surfaces 10SA of the image pickup members 10 are temporarily fixed to the second support substrate 61. That is, at least either of the first surfaces 10SA or the first upper surfaces 30SA1 are temporarily fixed to the second support substrate 61.

<Step S60> Wiring Layer Disposing Step

A wiring layer 20 is disposed, the wiring layer 20 including an insulation layer 22 (22A, 22B) and wirings 21 which respectively connect the external electrodes 14 of each image pickup member 10 with the core wire electrodes 32 of each terminal members 30. A wiring layer disposing step S60 includes a film forming step of forming a conductor layer 21M, which forms the wirings 21, is formed on the front surfaces of the external electrodes 14 and the front surfaces of the core wire electrodes 32.

By forming the wirings 21, each wiring 21 is brought into contact with the external electrode 14 and the core wire electrode 32 without other members being interposed between the wiring 21 and the external electrode 14 and between the wiring 21 and the core wire electrode 32 and hence, the wirings 21 are electrically connected with the external electrodes 14 and the core wire electrodes 32. Accordingly, the image pickup apparatus 1 can be easily manufactured, and the wirings 21 can be bonded with the external electrodes 14 and the core wire electrodes 32 with low electric resistance on a bonding interface and with high reliability.

Figure 9:
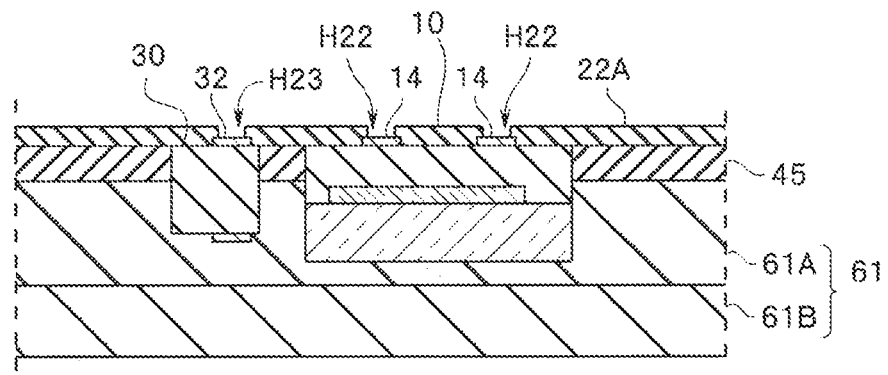
FIG. 9 is a cross-sectional view for describing the method for manufacturing the semiconductor device of the first embodiment.

As shown in FIG. 9, an insulation layer 22A is disposed, the insulation layer 22A having openings H22 and openings H23, the external electrodes 14 being exposed through the openings H22, the core wire electrodes 32 being exposed through the openings H23. The side surfaces of the protruding external electrodes 14 and the side surfaces of the protruding core wire electrodes 32 are covered by the insulation layer 22A. In the case where the external electrodes 14 or the core wire electrodes 32 are protruding electrodes, only the side surfaces of the protruding electrodes are covered by the insulation layer 22A. That is, at least either of the side surfaces of the external electrodes 14 or the side surfaces of the core wire electrodes 32 are covered by the insulation layer 22A.

Conversely, the image pickup apparatus where at least either of the side surfaces of the external electrodes 14 or the side surfaces of the core wire electrodes 32 are covered by the insulation layer 22A may be considered as an image pickup apparatus where the wirings 21 are formed, so that the wirings 21 are brought into contact with the external electrodes 14 and the core wire electrodes 32.

Figure 10:
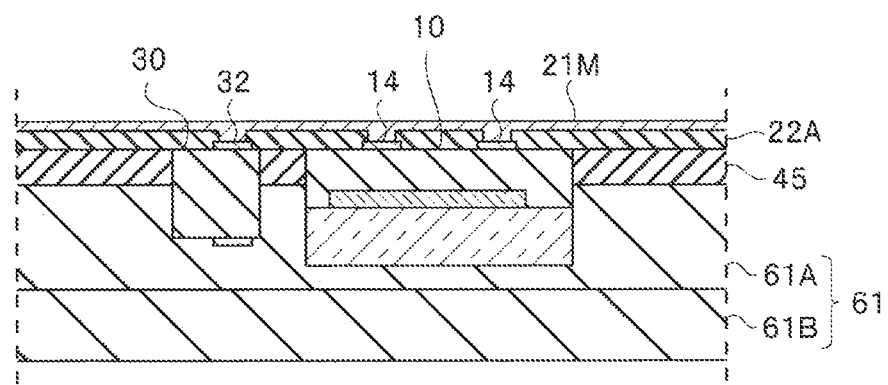
FIG. 10 is a cross-sectional view for describing the method for manufacturing the semiconductor device of the first embodiment.

As shown in FIG. 10, in the film forming step, the conductor layer 21M is formed in the openings H22, H23 and on the insulation layer 22A. The conductor layer 21M is formed on the front surface of the insulation layer 22A, on the front surfaces of the external electrodes 14 that are exposed through the openings H22, and on the front surfaces of the core wire electrodes 32 that are exposed through the openings H23 by a sputtering method or a vapor deposition method. The conductor layer 21M is made of copper, aluminum, or the like.

Figure 11:
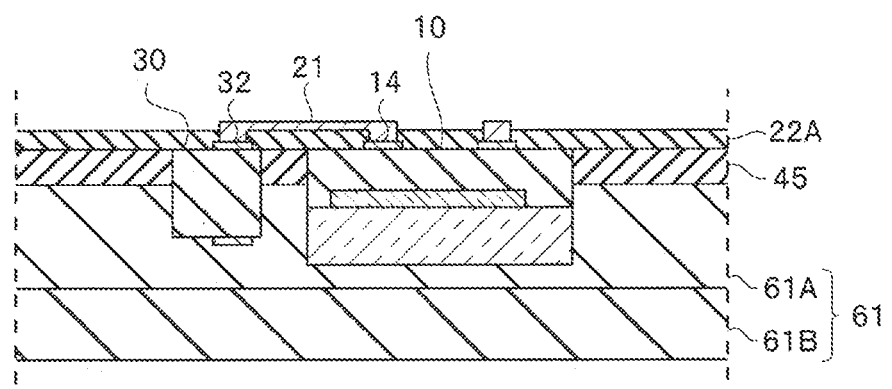
FIG. 11 is a cross-sectional view for describing the method for manufacturing the semiconductor device of the first embodiment.
Figure 12:
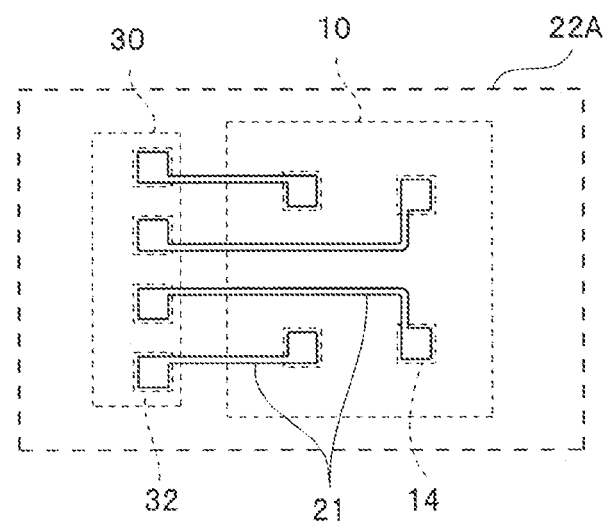
FIG. 12 is a plan view for describing the method for manufacturing the semiconductor device of the first embodiment.

By performing patterning on the conductor layer 21M, the wirings 21 as shown in FIG. 11 and FIG. 12 are formed, each wiring 21 connecting the external electrode 14 with the core wire electrode 32.

For forming the conductor layer 21M, after a base conductive film is formed, an electroplating method may be used with a plating mask having openings in the pattern of the wirings 21. In the case of the electroplating method, after the plating mask is detached, the base conductive film around the wirings 21 is removed.

Further, by disposing an insulation layer 22B that covers the wirings 21, the wiring layer 20 is formed. The wiring layer 20 may be a multi-wiring layer including the wirings 21 in two or more layers.

<Step S70> Second Separation Step

Figure 13:
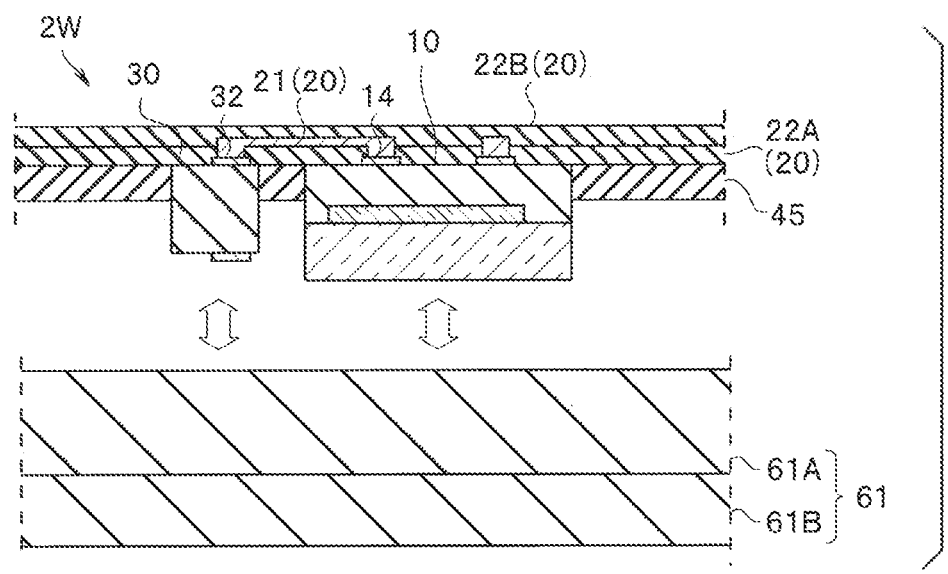
FIG. 13 is a cross-sectional view for describing the method for manufacturing the semiconductor device of the first embodiment.

As shown in FIG. 13, the main member wafer 2W including the wiring layer 20 is separated from the second support substrate 61.

<Step S80> Cable Bonding Step

Figure 14:
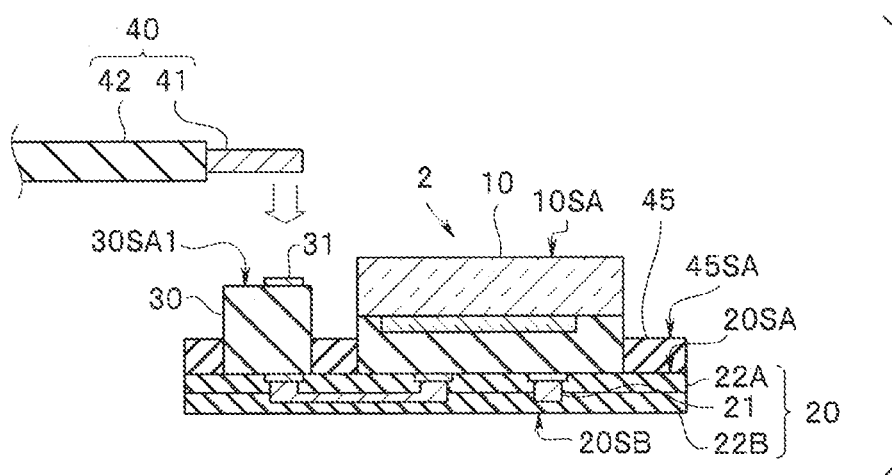
FIG. 14 is a cross-sectional view for describing the method for manufacturing the semiconductor device of the first embodiment.

As shown in FIG. 14, the main member wafer 2W including the wiring layer 20 is divided into a plurality of individual main members 2. The main members 2 are prepared by dividing (cutting) the main member wafer 2W into individual pieces. Therefore, the side surfaces of the resin layer 45 and the side surfaces of the wiring layer 20 are cut surfaces which are cut simultaneously and hence, the outer dimensions of an upper surface 45SA of the resin layer 45 are equal to the outer dimensions of a third surface 20SA (fourth surface 20SB) of the wiring layer 20.

Core wires 41 of electric cables 40 are bonded to the core wire terminals 31 of the terminal member 30 of the main member 2. Although not shown in the drawing, a prism 15 is caused to adhere to the first surface 10SA by using an adhesive agent 16.

The main member wafer 2W, to which the second support substrate 61 is caused to adhere, may be divided into individual pieces before the second separation step S70, and the electric cables 40 may be bonded to each terminal member 30 before individual second support substrates 61, obtained by dividing the main member wafer 2W into individual pieces, are separated. Further, the electric cables 40 may be bonded to each terminal member 30 before the main member wafer 2W is divided into individual pieces.

That is, a cut step of dividing the main member wafer 2W into the individual main members 2 is performed between the wiring layer disposing step S60 and the cable bonding step S80 or after the cable bonding step S80.

In the conventional technique, when a plurality of image pickup apparatuses are manufactured, a step of bonding an image pickup device to a wiring board is performed for each device. Therefore, the conventional technique is complicated.

In the case of the image pickup apparatus 1 of the present embodiment, a large number of main members 2 are manufactured in the form of a wafer and hence, the main members 2 can be easily manufactured. Needless to say, the main member 2 may be manufactured one by one.

Second Embodiment

An image pickup apparatus 1A and a method for manufacturing the image pickup apparatus 1A of the present embodiment are similar to the image pickup apparatus 1 and the method for manufacturing the image pickup apparatus 1, and have substantially the same advantageous effects and hence, constitutional elements having the same function are given the same reference symbols, and the repeated description will be omitted.

Figure 15:
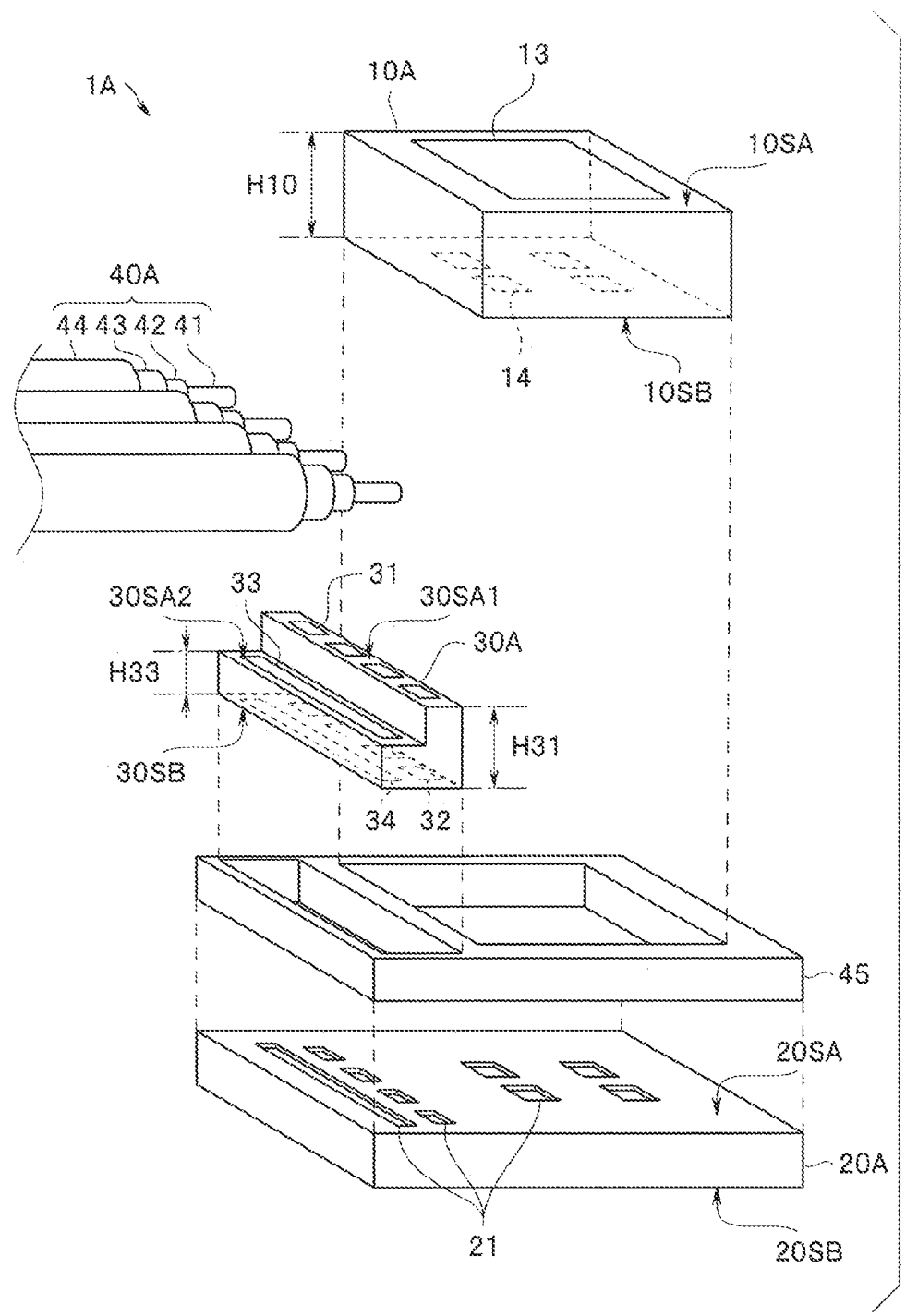
FIG. 15 is an exploded view of a semiconductor device of a second embodiment.

As shown in FIG. 15, an image pickup member 10A, which is the semiconductor member of the image pickup apparatus 1A, is an image pickup device where the first surface 10SA forms a light receiving surface and the thickness of the image pickup member 10A is H10. A cover glass or a prism may be caused to adhere to the light receiving surface of the image pickup member 10A.

A terminal member 30A has a second upper surface 30SA2, which is parallel to the first upper surface 30SA1. A height H33 of the second upper surface 30SA2 from the lower surface 30SB is smaller than a height H31 of the first upper surface 30SA1. A shield terminal 33 is disposed on the second upper surface 30SA2, and a shield electrode 34 is disposed on the lower surface 30SB. Although not shown in the drawing, the shield terminal 33 and the shield electrode 34 are connected with each other via a through wiring or the like.

Electric cable 40A are shielded cables each including the core wire 41, the first cover layer 42 that covers the core wire 41, a shield wire 43 that covers the first cover layer 42, and a second cover layer 44 that covers the shield wire 43.

The core wires 41 are respectively bonded with the core wire terminals 31, and the shield wires 43 are bonded with the shield terminal 33. The shield wires 43 of the plurality of electric cables 40A are bonded with one shield terminal 33, which is a common terminal. The shield wires 43 of the plurality of electric cables 40A may be respectively bonded with shield terminals 33.

Figure 16:
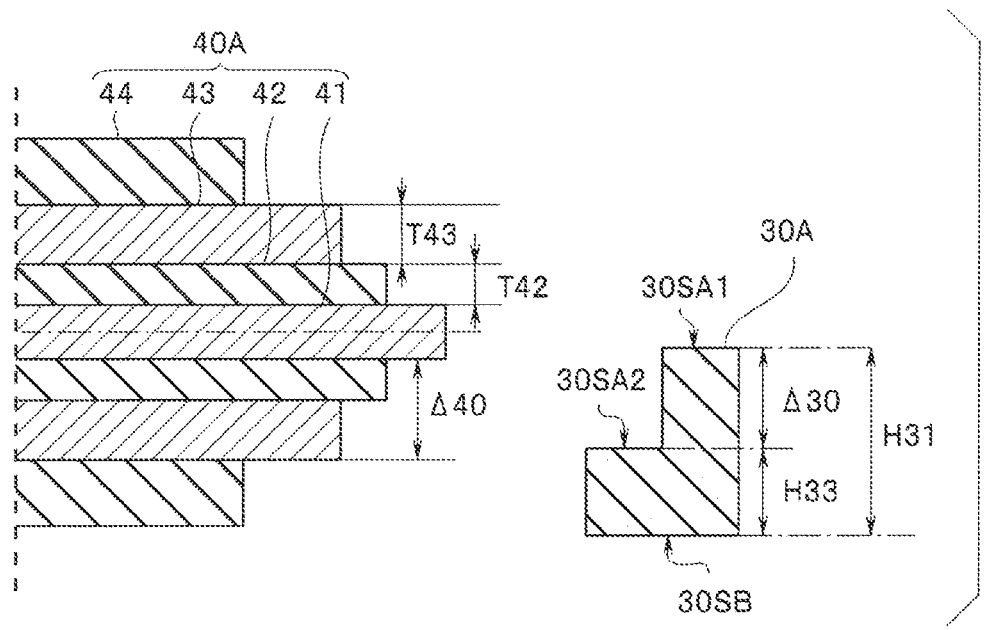
FIG. 16 is an exploded cross-sectional view of a portion of the semiconductor device of the second embodiment.

As shown in FIG. 16, a length 430 of the terminal member 30A from the first upper surface 30SA1 to the second upper surface 30SA2 is substantially equal to (for example, more than 75% and less than 125% of) a sum MO of a thickness T42 of the first cover layer 42 and a thickness T43 of the shield wire 43. That is, the terminal member 30A is set to a size that conforms to the electric cables 40A. In other words, the length 430 from the first upper surface 30SA1 to the second upper surface 30SA2 is set to a distance that allows the shield wires 43 to be in contact with the shield terminal 33 in a state where the core wires 41 are in contact with the core wire terminals 31.

In the image pickup apparatus 1A, the core wires 41 and the shield wires 43 of the electric cables 40A, which are shielded cables, can be easily bonded to the terminal member 30A.

Third Embodiment

An image pickup apparatus 1B and a method for manufacturing the image pickup apparatus 1B of the present embodiment are similar to the image pickup apparatus 1 and the method for manufacturing the image pickup apparatus 1, and have substantially the same advantageous effects and hence, constitutional elements having the same function are given the same reference symbols, and the repeated description will be omitted.

Figure 17:
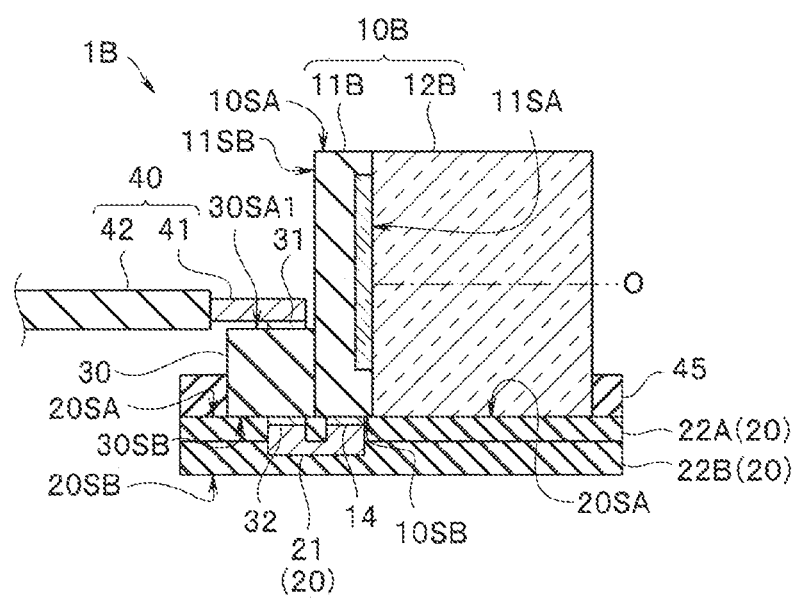
FIG. 17 is a cross-sectional view of a semiconductor device of a third embodiment.

As shown in FIG. 17, in the so-called vertical image pickup apparatus 1B, a semiconductor member is an image pickup member 10B where a cover glass 12B is caused to adhere to a light receiving surface 11SA of an image pickup device 11B orthogonal to the second surface 10SB. That is, the image pickup member 10B is disposed such that the direction of an optical axis O of the image pickup device 11B is parallel to the third surface 20SA of the wiring layer 20. Further, the first surface 10SA and the second surface 10SB form the side surfaces of the image pickup device 11B, each of the first surface 10SA and the second surface 10SB having an area smaller than the area of the light receiving surface 11SA.

To facilitate positioning of the terminal member 30 and the image pickup member 10B, an opposite surface 11SB on a side opposite to the light receiving surface 11SA of the image pickup member 10B may be in contact with the side surface of the terminal member 30.

The image pickup apparatus 1B is a vertical image pickup apparatus including no prism. However, the image pickup apparatus 1B has advantageous effects substantially equal to the advantageous effects of the horizontal image pickup apparatus 1, for example. Further, the vertical image pickup apparatus 1B has a shorter length than the horizontal image pickup apparatus 1.

Fourth Embodiment

A semiconductor device 1C and a method for manufacturing the semiconductor device 1C of the present embodiment are similar to the image pickup apparatus 1 and the method for manufacturing the image pickup apparatus 1, and have substantially the same advantageous effects and hence, constitutional elements having the same function are given the same reference symbols, and the repeated description will be omitted.

Figure 18:
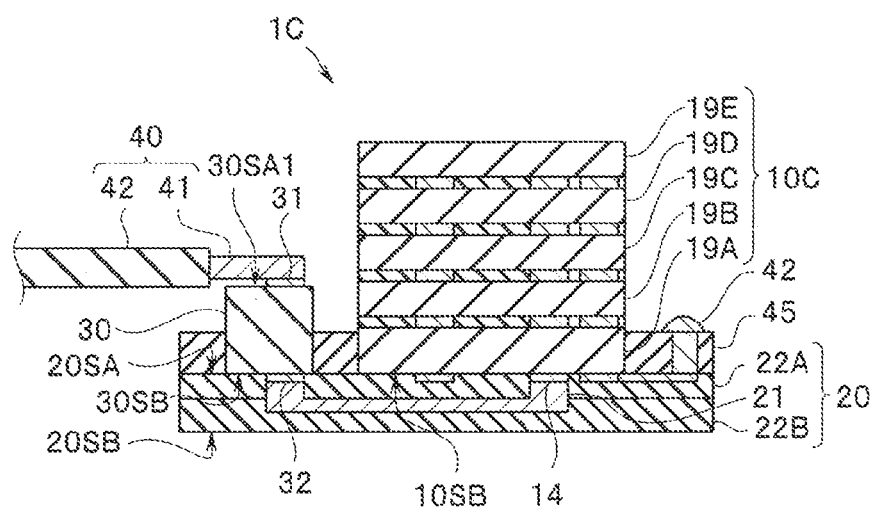
FIG. 18 is a cross-sectional view of a semiconductor device of a fourth embodiment.

The semiconductor device 1C shown in FIG. 18 includes a semiconductor member 10C.

The semiconductor member 10C performs processing on signals inputted to and outputted from the semiconductor member 10C via a terminal 30. For example, the semiconductor member 10C may be an AD conversion circuit, a memory, a transmission output circuit, a filter circuit, a thin film capacitor, a thin film resistor, or a thin film inductor that performs primary processing on an image pickup signal outputted from an image pickup device not shown in the drawing, or that performs processing on a control signal for controlling the image pickup device.

In the semiconductor device 1C, the wirings 21 are formed on the front surfaces of the external electrodes 14 of the semiconductor member 10C and hence, there is no possibility of heat and stress being applied to the semiconductor member 10C and hence, the semiconductor device 1C has high reliability. Further, the main member 2 to which the electric cables 40 are bonded is manufactured in the wafer process and hence, the semiconductor device 1C can be easily manufactured.

That is, the semiconductor device which includes the semiconductor member is not limited to an image pickup apparatus which includes an image pickup member. The semiconductor member may be, for example, an AD conversion circuit, a memory, a transmission output circuit, a filter circuit, a thin film capacitor, a thin film resistor, or a thin film inductor. The image pickup member may include the above-mentioned AD conversion circuit or the like.

Fifth Embodiment

An endoscope system 8 including the endoscope 9 of the present embodiment shown in FIG. 19 includes the endoscope 9, a processor 80, a light source device 81, and a monitor 82. The endoscope 9 includes an insertion portion 90, an operation portion 91, and a universal cord 92, and image pickup signals outputted from the image pickup apparatus 1 or the like, disposed at the distal end portion 90A of the insertion portion 90, are transmitted through the electric cables 40 inserted through the insertion portion 90. The universal cord 92 extends from the operation portion 91, and is connected to the processor 80 and the light source device 81 via connectors 93.

The insertion portion 90 of the endoscope 9 is inserted into the body cavity of the subject to shoot in-vivo images of the subject and to output image signals.

The proximal end portion of the insertion portion 90 of the endoscope 9 is provided with the operation portion 91 having various buttons which operate the endoscope 9.

The light source device 81 includes a white LED, for example. Illumination light emitted from the light source device 81 is guided to the distal end portion 90A through a light guide (not shown in the drawing) inserted through the universal cord 92 and the insertion portion 90, thus illuminating the object.

As has been described above, the image pickup apparatus 1 has high reliability and a small size and hence, the endoscope 9 has high reliability and a small diameter.

Needless to say, endoscopes 9A to 9C which include the image pickup apparatuses 1A, 1B or the semiconductor device 1C have advantageous effects of the image pickup apparatuses 1A, 1B or the semiconductor device 1C in addition to the advantageous effects of the endoscope 9.

The present invention is not limited to the above-mentioned embodiments and the like, and various changes, modifications, and combinations, for example, are conceivable without departing from the gist of the present invention.

What is claimed is:

1. A semiconductor device comprising:
    a semiconductor substrate having a first surface and a second surface opposed to the first surface, an external electrode being disposed on the second surface;
    a wiring layer having a third surface and a fourth surface opposed to the third surface, the wiring layer including an insulation layer and a wiring, the wiring being in electrical contact with the external electrode, the third surface being in contact with the second surface of the semiconductor substrate; and
    a resin layer disposed on the third surface of the wiring layer, an outer peripheral dimension of the resin layer being equal to an outer peripheral dimension of the wiring layer, the resin layer fixing the semiconductor substrate such that the resin layer does not cover the first surface.

2. The semiconductor device according to claim 1, wherein the semiconductor substrate has a semiconductor and a cover glass, and the semiconductor is an image pickup device to which the cover glass is adhered.

3. The semiconductor device according to claim 2, wherein a bottom surface of the image pickup device is disposed in a plane parallel to the third surface.

4. The semiconductor device according to claim 2, wherein the semiconductor substrate further has a light receiving surface connecting the first surface and the second surface, the image pickup device is disposed on the image pickup surface, and the image pickup surface is perpendicular to the third surface.

5. The semiconductor device according to claim 2, further comprising a prism having a prism surface configured to reflect an object image, the prism is disposed on the semiconductor substrate such that the object image is reflected by the prism surface towards the image pickup device.

6. The semiconductor device according to claim 5, wherein the prism is disposed on a surface of the cover glass.

7. The semiconductor device according to claim 1,
    wherein the semiconductor substrate comprises a first semiconductor substrate; and
    the semiconductor device further comprises at least one second semiconductor substrate stacked on the first semiconductor substrate.

8. The semiconductor device according to claim 1, further comprises a terminal member having a first upper surface and a lower surface opposed to the first upper surface, a core wire terminal being disposed on the first upper surface, and a core wire electrode being disposed on the lower surface;
    wherein the wiring is in electrical contact with the core wire electrode,
    the third surface is in contact with the lower surface of the terminal member; and
    the resin layer fixes the terminal member such that the resin layer does not cover the first upper surface.

9. The semiconductor device according to claim 8, wherein
    the terminal member has a second upper surface opposed to the lower surface, a shield terminal is disposed on the second upper surface, a shield electrode is disposed on the lower surface, the second upper surface is not covered by the resin layer, and
    a dimension from the first upper surface to the second upper surface is substantially equal to a sum of a thickness of a first cover layer covering a core wire of an electric cable and a thickness of a shield wire covering the first cover layer.

10. The semiconductor device according to claim 8, wherein the insulation layer covers one or more of a side surface of the external electrode or a side surface of the core wire electrode.

11. The semiconductor device according to claim 8, wherein a region of the wiring being in contact with at least the external electrode or the core wire electrode is made of a conductive material.

12. The semiconductor device according to claim 8, wherein the resin layer surrounds a periphery of the terminal member and a periphery of the semiconductor substrate.

13. The semiconductor device according to claim 12, wherein the resin layer is a single unitary layer.

14. The semiconductor device according to claim 8, wherein
    the semiconductor substrate has a semiconductor and a cover glass, and the semiconductor is an image pickup device to which the cover glass is adhered; and
    the resin layer surrounds a periphery of the terminal member and a periphery of the semiconductor substrate.

15. The semiconductor device according to claim 14, wherein a thickness of the resin layer in a direction normal to the first surface is smaller than a thickness of the semiconductor substrate in the direction.

16. The semiconductor device according to claim 8, wherein a thickness of the resin layer in a direction normal to the first surface is smaller than a thickness of the terminal member in the direction.

17. The semiconductor device according to claim 8, further comprising an electric cable including a core wire bonded to the core wire terminal.

18. The semiconductor device according to claim 17, wherein the electric cable includes a first cover layer that covers the core wire, a shield wire that covers the first cover layer, and a second cover layer that covers the shield wire, the shield wire being bonded with the shield terminal.

19. An endoscope including a semiconductor device, wherein
    the semiconductor device comprises:
        a semiconductor substrate having a first surface and a second surface opposed to the first surface, an external electrode being disposed on the second surface;
        a wiring layer having a third surface and a fourth surface opposed to the third surface, the wiring layer including an insulation layer and a wiring, the wiring being in contact with the external electrode, the third surface being in electrical contact with the second surface of the semiconductor substrate; and
        a resin layer disposed on the third surface of the wiring layer, an outer peripheral dimension of the resin layer being equal to an outer peripheral dimension of the wiring layer, the resin layer fixing the semiconductor substrate such that the resin layer does not cover the first surface.

20. The endoscope according to claim 19, wherein the semiconductor device further comprises:
   a terminal member having a first upper surface and a lower surface opposed to the first upper surface, a core wire terminal being disposed on the first upper surface, and a core wire electrode being disposed on the lower surface;
   wherein the wiring is in contact with the core wire electrode,
   the third surface is in electrical contact with the lower surface of the terminal member; and
   the resin layer fixes the terminal member such that the resin layer does not cover the first upper surface; and
the endoscope further comprises an electric cable including a core wire bonded to the core wire terminal.

\* \* \* \* \*